United States Patent [19]

Braun et al.

[11] Patent Number: 4,753,834
[45] Date of Patent: Jun. 28, 1988

[54] NONWOVEN WEB WITH IMPROVED SOFTNESS

[75] Inventors: Ralph V. Braun, Roswell; Jon R. Butt, Woodstock; Henry L. Griesbach, III, Atlanta; Robert J. Phelan, Woodstock, all of Ga.; Edward H. Ruscher, Appleton, Wis.; Lin-Sun Woon, Appleton, Wis.

[73] Assignee: Kimberly-Clark Corporation, Neenah, Wis.

[21] Appl. No.: 35,263

[22] Filed: Apr. 2, 1987

Related U.S. Application Data

[63] Continuation of Ser. No. 785,365, Oct. 7, 1985, abandoned.

[51] Int. Cl.$^4$ .............................................. B65D 65/28
[52] U.S. Cl. ..................................... 428/74; 156/62.4; 156/167; 156/290; 156/308.4; 264/123; 264/177.15; 264/210.8; 264/296; 264/DIG. 75; 428/76; 428/198; 428/286; 428/296; 428/311.5; 428/319.3; 428/338; 428/339; 428/397; 428/401; 604/366; 604/378
[58] Field of Search .................... 156/167, 240, 308.4, 156/62.4; 264/123, 177 F, 210.8, 296, DIG. 75; 428/74, 76, 198, 286, 296, 311.5, 319.3, 338, 339, 397, 401; 604/366, 378

[56] References Cited

U.S. PATENT DOCUMENTS

| Re. 31,599 | 6/1984 | Rasen et al. . |
|---|---|---|
| 1,786,669 | 12/1930 | Manning . |
| 2,121,802 | 6/1938 | Kleist et al. . |
| 2,188,332 | 1/1940 | Carothers . |
| 2,331,945 | 10/1943 | Pazsiczky . |
| 2,336,743 | 12/1943 | Manning . |
| 2,336,745 | 12/1943 | Manning . |
| 2,411,660 | 11/1946 | Manning . |
| 2,437,263 | 3/1948 | Manning . |
| 2,456,922 | 12/1948 | Cogovan . |
| 2,508,462 | 5/1950 | Marshall . |
| 2,522,527 | 9/1950 | Manning . |
| 2,604,667 | 7/1952 | Hebeler . |
| 2,620,853 | 12/1952 | Boese . |

(List continued on next page.)

FOREIGN PATENT DOCUMENTS

| 1938 | 1/1970 | Japan . |
|---|---|---|
| 12860 | 1/1980 | Japan . |
| 128006 | 10/1980 | Japan . |
| 42980 | 4/1981 | Japan . |
| 50001 | 11/1981 | Japan . |
| 107044 | 11/1981 | Japan . |
| 42916 | 3/1982 | Japan . |
| 61712 | 4/1982 | Japan . |
| 25645 | 5/1982 | Japan . |
| 37961 | 3/1983 | Japan . |
| 36741 | 2/1984 | Japan . |
| 47446 | 3/1984 | Japan . |
| 94609 | 5/1984 | Japan . |
| 204919 | 11/1984 | Japan . |
| 223314 | 12/1984 | Japan . |
| 228019 | 12/1984 | Japan . |
| 228042 | 12/1984 | Japan . |
| 4575 | 1/1985 | Japan . |
| 134012 | 7/1985 | Japan . |
| 185810 | 9/1985 | Japan . |
| 51565 | 11/1985 | Japan . |
| 12907 | 1/1986 | Japan . |
| 83307 | 4/1986 | Japan . |
| 83308 | 4/1986 | Japan . |
| 83309 | 4/1986 | Japan . |
| 816877 | 7/1959 | United Kingdom . |
| 924087 | 4/1963 | United Kingdom . |

OTHER PUBLICATIONS

Scardino et al., "Engineering Properties of Fibers for Nonwoven Fabrics", *Nonwoven Industry*, Apr., 1983, pp. 18–22.

*Primary Examiner*—James C. Cannon
*Attorney, Agent, or Firm*—Patrick C. Wilson

[57] ABSTRACT

Nonwoven webs are disclosed which comprise monofilaments or fibers of a thermoplastic material. Basically, the improvement comprises the use of monofilaments or fibers which have a bilobal shaped cross-section. Nonwoven webs made according to this invention are particularly suited to be used for liners for disposable diapers as well as wraps for catamenial devices. Methods are also disclosed for producing such nonwoven webs.

55 Claims, 2 Drawing Sheets

U.S. PATENT DOCUMENTS

| | | |
|---|---|---|
| 2,644,779 | 7/1953 | Manning . |
| 2,688,380 | 9/1954 | MacHenry . |
| 2,810,426 | 10/1957 | Till et al. . |
| 2,816,349 | 12/1957 | Pamm et al. . |
| 2,825,120 | 3/1958 | Smith . |
| 2,861,319 | 11/1958 | Breen . |
| 2,945,739 | 7/1960 | Lehmicke . |
| 3,028,623 | 4/1962 | Labino . |
| 3,063,454 | 11/1962 | Coates et al. . |
| 3,109,220 | 11/1963 | McKinney et al. . |
| 3,109,278 | 11/1963 | Gibson . |
| 3,117,906 | 1/1964 | Tanner . |
| 3,154,836 | 11/1964 | Hoag et al. . |
| 3,164,949 | 1/1965 | Pitzl . |
| 3,219,739 | 11/1965 | Breen et al. . |
| 3,266,969 | 8/1966 | Makansi . |
| 3,297,807 | 1/1967 | Settele . |
| 3,303,169 | 2/1967 | Pitzl . |
| 3,314,840 | 4/1967 | Lloyd et al. . |
| 3,322,607 | 5/1967 | Jung . |
| 3,360,421 | 12/1967 | Sands . |
| 3,366,722 | 1/1968 | Tessier . |
| 3,379,811 | 4/1968 | Hartmann et al. . |
| 3,396,071 | 8/1968 | Couzens . |
| 3,402,548 | 9/1968 | Wininger et al. . |
| 3,420,235 | 1/1969 | Harmon . |
| 3,441,468 | 4/1969 | Sigget et al. . |
| 3,492,389 | 1/1970 | Port et al. . |
| 3,502,763 | 3/1970 | Hartmann . |
| 3,508,390 | 4/1970 | Bognall et al. . |
| 3,509,009 | 4/1970 | Hartmann . |
| 3,528,129 | 9/1970 | Hartmann . |
| 3,533,904 | 10/1970 | Jurkiewitsch . |
| 3,547,763 | 12/1970 | Hoffman et al. . |
| 3,554,854 | 1/1971 | Hartmann . |
| 3,630,816 | 12/1971 | Parker . |
| 3,692,618 | 9/1922 | Dorschner et al. . |
| 3,758,373 | 9/1973 | Rich . |
| 3,837,995 | 9/1974 | Floden . |
| 3,841,953 | 10/1974 | Lohkamp et al. . |
| 3,855,045 | 12/1974 | Brock . |
| 3,855,046 | 12/1974 | Hansen et al. . |
| 3,949,127 | 4/1976 | Ostermeier et al. . |
| 3,968,307 | 7/1976 | Matsui et al. . |
| 4,013,816 | 3/1977 | Sabee et al. . |
| 4,039,711 | 8/1977 | Newman . |
| 4,041,203 | 8/1977 | Brock et al. . |
| 4,041,689 | 8/1977 | Duncan et al. . |
| 4,054,709 | 10/1977 | Belitsin et al. . |
| 4,085,175 | 4/1978 | Keuchel . |
| 4,091,140 | 5/1978 | Harmon . |
| 4,100,319 | 7/1978 | Schwartz . |
| 4,107,364 | 8/1978 | Sisson . |
| 4,211,816 | 7/1980 | Booker et al. . |
| 4,287,251 | 9/1981 | King et al. . |
| 4,304,234 | 12/1981 | Hartmann . |
| 4,315,905 | 2/1982 | Mason et al. . |
| 4,333,979 | 6/1982 | Sciaraffa et al. . |
| 4,340,563 | 7/1982 | Appel et al. . |
| 4,350,006 | 9/1982 | Okamoto et al. . |
| 4,359,445 | 11/1982 | Kane et al. . |
| 4,363,845 | 12/1982 | Hartmann . |
| 4,379,192 | 4/1983 | Wahlquist . |
| 4,405,297 | 9/1983 | Appel et al. . |
| 4,405,686 | 9/1983 | Kuroda et al. . |
| 4,434,204 | 2/1984 | Hartmann et al. . |
| 4,436,780 | 3/1984 | Hotchkiss et al. . |
| 4,469,734 | 9/1984 | Minto et al. . |
| 4,519,798 | 5/1985 | Dinius . |
| 4,537,822 | 8/1985 | Nanri et al. . |

# NONWOVEN WEB WITH IMPROVED SOFTNESS

This is a continuation of co-pending application Ser. No. 785,365, filed on Oct. 7, 1985, now abandoned.

BACKGROUND OF THE INVENTION

The present invention relates to a nonwoven web having improved softness. More particularly, the present invention relates to a nonwoven web comprised of fibers having a bilobal cross-section as well as the method of making such a nonwoven web.

Nonwoven materials are, of course, well known in the art. Such materials were developed primarily in the 1950's and 1960's, although at least one reference dates back to 1943 (see, e.g., U.S. Pat. No. 2,336,743 to Manning).

One of the most significant commercial applications of nonwoven webs is in the fabrication of disposable products intended for a single use. Typical of such products are disposable diapers, feminine care products, surgical gowns, industrial wipes, and the like. Because the nonwoven web is intended as a cloth substitute in these applications, extensive effort has been expended to improve the properties of the nonwoven web to more nearly approximate those of cloth. Of particular interest has been the softness of the nonwoven web, that is, lowering the resistance of the web to folding or bending as well as improving the "hand" or softness of touch. Another important area has been the improvement of the nonwoven web's tensile strength or tear resistance. With the few exceptions noted below, these efforts to improve the properties of nonwoven webs has focused almost exclusively on the use of fibers having a circular cross-section.

U.S. Pat. No. 2,336,743 to Manning describes a method and apparatus for solution spinning or melt spinning nonwoven fabrics. According to the specification, the spinning material can be extruded through orifices in the spinneret, which orifices may be slits, circular, or of other cross-section.

U.S. Pat. No. 3,314,840 to Lloyd et al. relates to a process and apparatus for producing a nonwoven fabric. Although the disclosure appears to relate primarily to solution spinning, it does not appear to exclude melt spinning. The spinneret preferably has circular or slit openings, although such openings may have other shapes such as circles, triangles, crescents, etc.

U.S. Pat. No. 3,508,390 to Bagnall et al. relates to a modified filament and fabrics produced therefrom. While the emphasis of the disclosure is on the preparation of conventional knitted fabrics, nonwoven fabrics are also mentioned. The filament has a cross-section consisting of three integrally joined, substantially symmetrical legs, thereby forming a substantially uniform Y-shaped cross-section having defined dimensions.

U.S. Pat. No. 3,509,009 to Hartmann relates to a nonwoven fabric which is prepared by meltspinning fiber-forming high polymers into a directed gas current of high velocity to produce a uniform nonwoven fabric of great strength. While the filaments produced in accordance with the described invention are typically of circular cross-section, other cross-sections are mentioned, such as star-shaped, Y-shaped, or a combination thereof.

An apparatus for producing nonwoven fleeces is described in U.S. Pat. No. 3,528,129 also to Hartmann. The patent appears to be an improvement of an existing apparatus by specifying holes in the spinneret which have a branched cross-section. Y-shaped and T-shaped holes are specifically mentioned.

Finally, U.S. Pat. No. 3,630,816 to Parker relates to nonwoven sheets made from filaments having a rectangular cross-section. The rectangular cross-section of these filaments is specified to have an aspect ratio of at least 3:1.

SUMMARY OF THE INVENTION

It is a general object of the present invention to provide a nonwoven web with improved softness. It is also a general object of the present invention to provide a method of producing such a nonwoven web. It is a more specific object of the present invention to provide a nonwoven liner for a disposable diaper which has improved softness. It is another specific object of the present invention to provide a nonwoven wrap for a catamenial device which has improved softness.

These and other objects are accomplished by the present invention by providing a nonwoven web comprising a plurality of fibers or monofilaments of a thermoplastic material, each monofilament having a bilobal cross-section, as well as a method for producing such a nonwoven web. By the term "bilobal" the applicants intend to refer to a shape including an elongate substantially rectangular portion which has at each of its furthest separated ends an enlarged portion which is typically circular and which portion has a diameter greater than the thickness of the rectangle. It has been found by the present inventors that a nonwoven web made with such bilobal shaped monofilaments provides remarkably increased softness as well as other desirable properties.

In accordance with one of the preferred embodiments, the nonwoven web comprises a plurality of substantially identically prepared continuous and substantially randomly deposited monofilaments of a thermoplastic polymer. In addition, the web is stabilized by discrete compacted areas of thermally induced filament bonds extending through a major portion of the thickness of the article, with these compacted areas distributed in an intermittent regular pattern and constituting from about 10 to about 30 percent of the area of the web. Also in accordance with this preferred embodiment, the thermoplastic material is a polyolefin. Most preferably, the polyolefin is polypropylene, polyethylene, or an ethylene-propylene copolymer.

In accordance with another of the preferred embodiments, a nonwoven liner for a disposable diaper is constituted similarly to the preferred embodiment mentioned immediately above, with the addition of a wetting agent to the polyolefin monofilaments to thereby make the liner which would otherwise be hydrophobic, somewhat hydrophillic or wettable. This can be done by mixing a wetting agent with the polymer before it is extruded or, more preferably, it can be done by applying a solution of the wetting agent to the nonwoven web after it is formed.

In accordance with still another of the preferred embodiments, the nonwoven wrap for a catamenial device is likewise made wettable in the same manner as the preferred embodiment of the nonwoven liner for a disposable diaper.

In accordance with yet another of the preferred embodiments, the method of the present invention includes the following steps. The polymer is preferably extruded while in a melted state through a spinneret plate with a multiplicity of holes of the desired bilobal cross-section, thereby producing a plurality of monofilaments with a bilobal cross-section. These monofilaments are then drawn, preferably pneumatically. After drawing, the monofilaments are laid down on a moving belt. At this point, the monofilaments are essentially randomly oriented with respect to each other. It is then preferable to slightly compact the monofilaments together by passing through a pair of oppositely rotating rollers. The web is then stabilized by passing it through a pair of heated rollers the first of which has a smooth surface, and the second of which has a raised pattern. As a result, the web becomes thermally bonded in discrete areas arranged in a pattern which corresponds with the raised pattern of the one heated roller. Preferably, the pattern of thermally bonded areas is formed so as to constitute between about 10 and 30 percent of the surface of the nonwoven web.

DETAILED DESCRIPTION

In its broadest terms, the present invention comprehends a nonwoven web comprising a plurality of monofilaments or fibers of a thermoplastic material, each of which monofilaments of fibers have a bilobal cross-section. In particular, the cross-sectional shape of these monofilaments can be described as including an elongate substantially rectangular portion which has at each of its furthest separated ends an enlarged, and typically circular portion which has a diameter greater than the thickness of the rectangle. This shape could also be described as a "dog bone" or "dumbbell".

In general, such a web can be prepared from noncontinuous fibers, continuous monofilaments, or a combination thereof. At present, continuous monofilaments, such as those produced by spunbonding techniques, are preferred. Alternatively, melt blowing techniques which produce noncontinuous fibers may be used.

The thermoplastic material can be any material which is capable of being spun or blown into fibers or monofilaments. While it is contemplated to use materials such as glass, as a practical matter, it is preferred to use polymeric materials. Examples of such polymers, by way of illustration only, include polyolefins, polyamides, polyesters, polyvinyl acetate, polyvinyl chloride, polyvinyl alcohol, polyurethanes, polyacrylonitrile, polymethyl methacrylate, polyethyl acrylate, cellulose acetate, viscose, and the like. In addition, the thermoplastic material can be a homopolymer, a copolymer, or a blend or two or more polymers. At present, homopolymers, copolymers, and polymer blends of the polyolefins are preferred, with copolymers and homopolymers being more preferred. The most preferred homopolymers are polypropylene and polyethylene, and the most preferred co-polymer is an ethylene/propylene copolymer.

Figure 1:
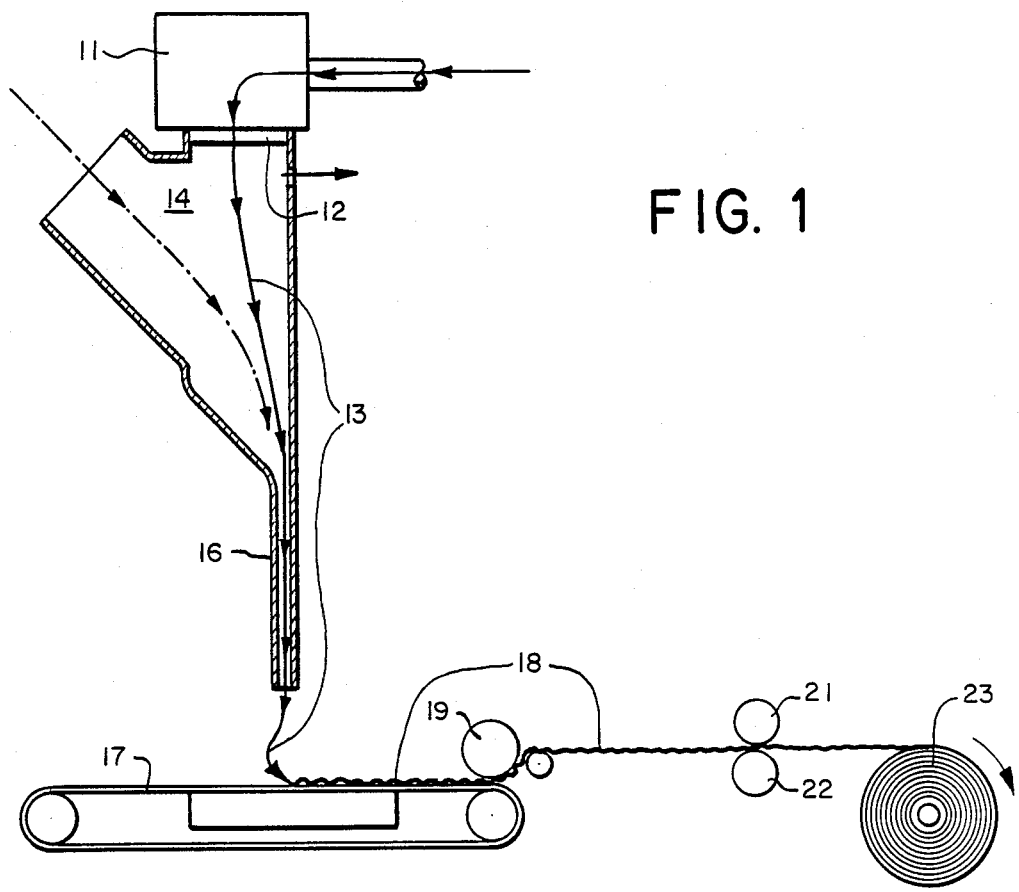
FIG. 1 is a schematic diagram of the preferred apparatus for producing the nonwoven web of the present invention.

FIG. 1 is a schematic diagram showing the preferred apparatus for forming such polymers into nonwoven webs. This apparatus is made in accordance with the teachings of U.S. Pat. No. 4,405,297 and operated in accordance with the teachings of U.S. Pat. No. 4,340,563, both to Appel and Morman, the entire disclosures of which are incorporated herein by reference. While this is the preferred apparatus and method of forming the nonwoven web, other apparatus and methods are also available. For example, an alternative embodiment forms a nonwoven web with the apparatus and method described in U.S. Pat. No. 3,692,618, to Dorschner et al., the entire disclosure of which is also incorporated herein by reference.

Briefly, the apparatus shown in FIG. 1 includes a spinneret box 11 which receives the polymer in a melted state. The temperature of the polymer melt is selected so as to make it sufficiently fluid for spinning. For example, when polypropylene is being spun, the preferred temperature is about 460° F. Pressure is applied to the polymer melt to thereby push it through the holes or orifices in the spinneret plate 12 to thereby form a curtain of monofilaments 13. The curtain 13 falls through a quench chamber 14 wherein it is contacted by quench air 26. The quench air is supplied at a relatively low pressure, but such that is sufficient pressure to also cause a degree of drawing of the monofilaments when they pass through the drawing nozzle 16. Upon exiting the lower end of the drawing nozzle 16, the monofilaments are laid down on a moving foraminous surface 17, such as an endless screen or belt, to form a nonwoven web 18. The web 18 passes through a pair of compacting rollers 19 and 20 which slightly compact the filaments in the web to thereby increase the web's integrity and aid in further processing.

The web 18 next passes through the two heated bonding rolls 21 and 20. These rolls are preferably made and operated in accordance with the teachings of U.S. Pat. No. 3,855,046, to Hansen and Pennings, the entire disclosure of which is incorporated herein by reference. Briefly, the apparatus and process described therein includes the use of two rolls 20 and 21, at least one of which and preferably both of which are heated. The lower roll has a smooth surface while the upper roll 21 includes a raised intermittent pattern on its surface. As the web 18 passes between these two heated rolls, the web becomes stabilized by the formation of discrete compacted areas of thermally induced filament bonds which extend through a major portion of the thickness of the web. These compacted areas are distributed in an intermittent pattern corresponding to the raised pattern of the roll 21 and provide unbonded filament spans therebetween.

Figure 5A:
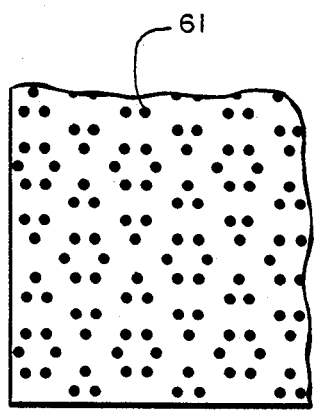
FIGS. 5a–c represent various patterns of intermittent heat bonding which can be applied to the nonwoven web of the present invention.
Figure 5B:
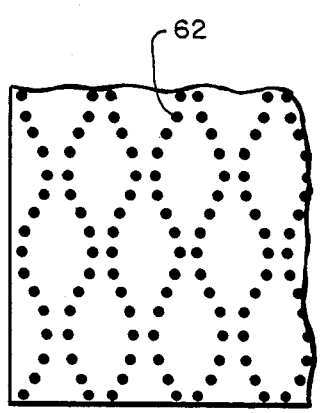
Figure 5C:
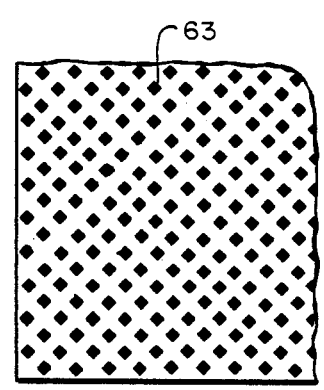

FIGS. 5a–5c illustrate three patterns which can be used on the roll 21 which produce the same patterns on the nonwoven web 18. FIG. 5a includes circular areas 61 arranged in hexagons and triangles. FIG. 5b includes circular areas 62 arranged in a repeating hourglass configuration. FIG. 5c, which is the presently preferred pattern, includes equilateral diamond shaped areas 63 which are arranged in staggered rows.

Two parameters of concern in regard to the specific pattern that is used are the size of the compacted areas formed and the distance between the areas. These two parameters together affect the percentage of area on the web which becomes bonded. It is important that the percentage of bonded area be great enough to insure sufficient integrity of the web for its intended use. In addition, it is important that the percentage of bonded area not be too great, as a higher bonded area usually produces a web with reduced softness. At present, it is preferred to have a bonded area between about 10 and about 30 percent of the surface area of the web. A range of about 12 to about 20 percent bonded area is more preferred, while about 17 percent is most preferred.

Another important factor relating to the bonding of the web is the temperature at which the rolls 21 and 22 are maintained. Naturally temperatures below a certain point for each polymer will not effect any bonding, while temperatures above another point will melt too much of the web. Also, it has been observed the temperature of the rolls can affect both the tensile strength as well as the softness of the web produced. In particular, within a certain range, higher temperatures will produce a web with higher tensile strength. However, these same higher temperatures can produce a web with decreased softness. This is likely due to a higher or lower degree of bonding which occurs within this range of temperatures. That is, the higher temperatures likely result in more and stronger interfilament bonding which is beneficial to tensile strength and somewhat detrimental to softness. At present, the preferred bonding temperature when using polypropylene is between about 220° and about 320° F. A temperature of about 275° F. is most preferred.

The inventors have observed that the nonwoven webs made with bilobal monofilaments can generally be bonded at a lower temperature than those with circular monofilaments. This is an important advantage in that typically softer webs result from lower bonding temperatures.

In alternative embodiments, the web may be stabilized by other methods. For example, the nonwoven web may be heat bonded in another way or as part of another process in a different fabrication line. Also, the nonwoven web may be stabilized by addition of an adhesive which would cause some interfilament bonding. In addition, techniques are known in the art for stabilizing a nonwoven web by increasing the entanglement of the filaments to thereby create a degree of interfilament bonding.

Referring again the FIG. 1 and the preferred embodiment, after the web 18 is bonded by rolls 21 and 22, it is wound on the wind up roll 23. Alternatively, it may be desirable to design this apparatus to connect with the fabrication line for an end product.

Figure 2:
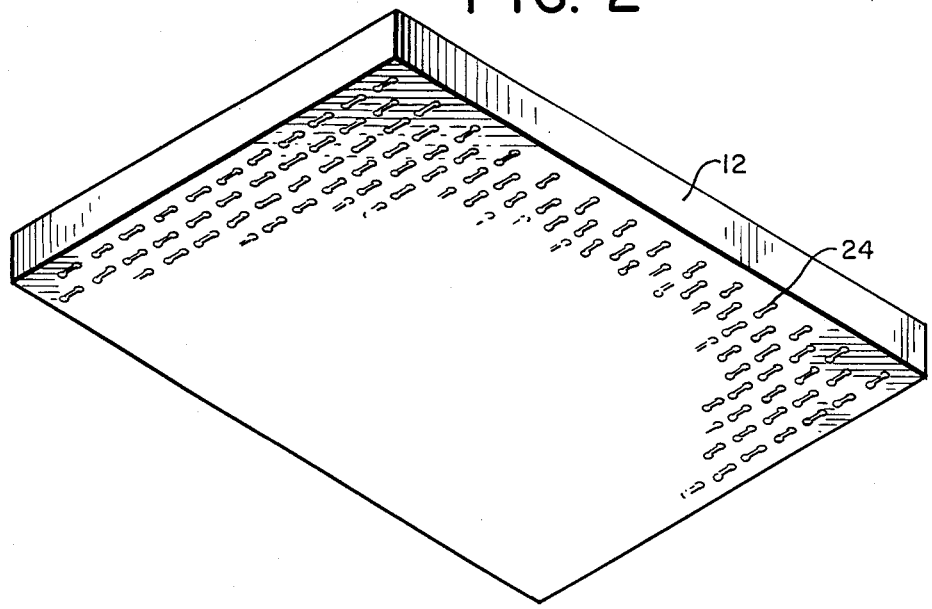
FIG. 2 shows a bottom perspective view of a spinneret plate with bilobal shaped orifices to thereby extrude monofilaments of bilobal cross-section.

The basis weight of the nonwoven web produced can be readily varied depending on the intended use of the web. For example, the nonwoven web can be made from about 0.3 to about 3.0 oz./square yard. A preferred basis weight for a disposable diaper liner is about 0.8 oz./square yard and a preferred basis weight for a nonwoven wrap for a catamenial device is about 0.4 oz./square yard FIG 2 is a bottom perspective view of the spinneret plate 12 with bilobal shaped orifices 24. It is through these orifices 24 that the polymer is extruded. The monofilaments produced consequently have a cross-section with a bilobal, "dog bone" or "dumbbell" shape.

The spinneret plate 12 is made with a width slightly greater than the width to be produced. The preferred width of the web will vary depending on the end use to made of it. For example, a nonwoven web made to be used as a liner for disposable diapers is preferably about 12.5 inches wide.

The number of orifices is selected and the orifices are arranged in the plate at the prescribed spacing in such a way so as to provide the desired density of filaments in the web. At present, it is preferred to have between about 30 and about 100 orifices in the spinneret plate per inch of web width. Most preferable is about 85 orifices per inch of web width. For example, a 12 inch spinneret plate, i.e. one that will form a 12 inch wide nonwoven web, there are most preferably 1020 orifices.

Figure 3:
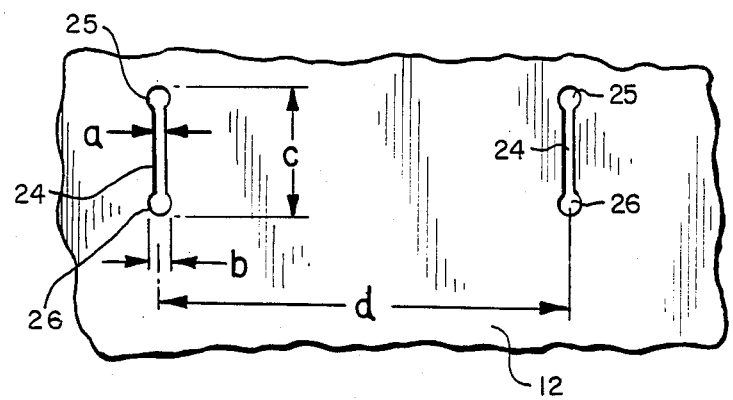
FIG. 3 is a bottom and enlarged view of two of the bilobal shaped orifices of the spinneret plate of FIG. 2.

FIG. 3 is an enlarged view showing the preferred configuration of two of the orifices 24 of the spinneret plate 12. The dimensions and proportions of the bilobal orifices are not known to be critical, provided that they produce monofilaments which have the bilobal shaped cross-section according to the present invention. Currently, the preferred configuration of the orifice is as follows. The shortest dimension is the thickness of the elongate portion a. The diameter b of the substantially circular portions 25 and 26 is approximately twice that of the thickness a. The length c of the orifice 24 is approximately ten times that of the thickness a. In the most preferred embodiment, the thickness a is 0.215 mm, the diameter b is 0.430 mm and the length c is 2.15 mm. Certainly, these dimensions and proportions can be varied in alternative embodiments depending on factors such as the specific polymer which is extruded and the desired properties of the nonwoven web.

As mentioned, the preferred spacing between orifices will depend on the density of the nonwoven web to be produced. In the most preferred embodiment, the space d between orifices is 7.25 mm. Also, the preferred orientation of the orifices is such that all of the orifices are arranged parallel to each other and that their length c is aligned in the direction in which the belt 17 moves (i.e. machine direction).

Figure 4:
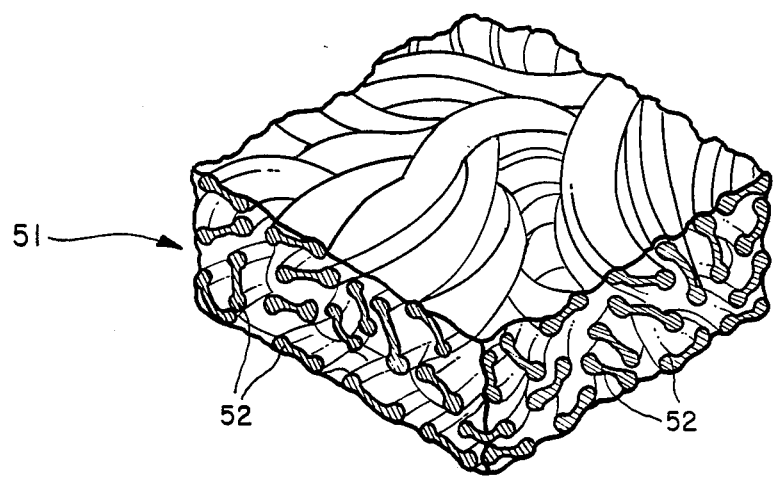
FIG. 4 is an illustration in partial cross-section of nonwoven fabric according to the present invention with monofilaments of bilobal cross-section.

FIG. 4 is an illustration of a section of nonwoven web 51 made according to the present invention. As can be seen the web comprises a number of continuous monofilaments 52 which are randomly oriented with respect to each other. It is desirable for the monofilaments to undergo a high degree of looping and overlapping in the web. These properties are influenced by factors such as the density of the monofilaments that are laid down, the speed at which the monofilaments are laid down, etc.

As can be seen, the monofilaments of this web 51 each have a bilobal cross-section. The dimensions of the bilobal cross-section are not known to be critical, provided that the basic features of such cross-section are present. That is, the cross-section of the monofilaments includes a substantially rectangular portion which has at each of its furthest separated ends an enlarged portion which typically is substantially circular.

As mentioned above, the monofilaments are drawn after being extruded through the spinneret plate 12. As a result, they typically have dimensions less than that of the orifices 24. The amount of this reduction will depend on factors such as the specific polymer extruded, the rate of quenching the monofilaments, the drawing force applied to the monofilaments, etc. In the preferred embodiment wherein polypropylene is used, the monofilaments typically end up with a cross-section length of between about 30 and about 60 microns. Most preferably, the cross-section length is about 40 microns, although this will vary depending on the desired properties of the nonwoven web.

Figure 6:
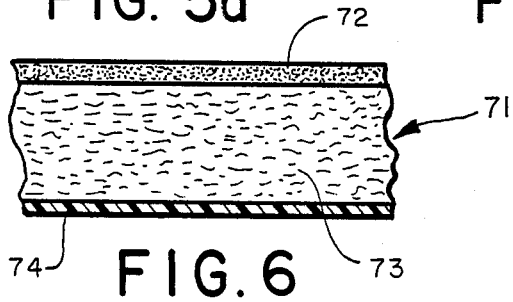
FIG. 6 is a cross section of a disposable diaper made with the nonwoven liner of the present invention.

FIG. 6 is a cross-section through a disposable diaper 71. The nonwoven liner 72 is positioned on the side of the diaper 71 which will be placed next to the infant's body. The major portion of the diaper consists of a layer 73 of an absorbent material such as fluffed cellulose pulp. Naturally, this layer 73 is intended to absorb moisture. In addition, a moisture impermeable layer 74 is included.

An important property of the liner 72 is its softness. In particular, it is important for the liner 72 to be both extremely pliable and soft to the touch in consideration of the infant's comfort. The present inventors were somewhat surprised to observe that a nonwoven liner made with the bilobal cross-section of the present invention exhibited remarkably improved softness over the prior art nonwoven liners made with monofilaments of circular cross-section.

One test which the inventors have used to evaluate the softness of nonwoven webs is called the "Smeltnik Stiffness Test". In this test a piece of nonwoven fabric is placed on top of an open cylinder. A hemispherical probe with a diameter slightly less than the inside diameter of the cylinder is then dropped from a standard height to thereby push the nonwoven fabric down into the cylinder. The distance that the probe travels into the cylinder is then measured and recorded as an indication of the softness, i.e. pliability or drapability of the fabric. As a comparison, a nonwoven diaper liner made with circular monofilaments recorded a distance of 155 mm into the cylinder, whereas a nonwoven diaper liner made with monofilaments of the same material but having a bilobal cross-section recorded a distance of 370 mm. Thus, a dramatic increase of the softness of the fabric was shown.

Another aspect of softness which is important particularly in diaper liners is the "hand" or softness to the touch. While a specific test for this property is not presently available to the inventors, they as well as others have observed an increased softness to the touch of the nonwoven web made with the monofilaments of bilobal cross-section.

Another property of a nonwoven web which is particularly important when the web is used as a liner for a disposable diaper is the wettability of the liner. Depending on the design of the diaper, it is usually desirable to have the liner be at least partially wettable in order to facilitate passage of the moisture through to the absorbent layer. However, many of the polymers which are suitable to make nonwoven webs are hydrophobic. Specifically, the two most preferred polymers, polypropylene and polyethylene are completely hydrophobic. As a result, it may be desirable to take steps to increase the wettability of nonwoven webs made with these polymers.

It is known in the art that wettability can be increased by the addition of wetting agents such as surfactants. Particularly, cationic, anionic, and nonionic surfactants may be added to materials to thereby make the material wettable. In one preferred embodiment of the present invention, the polypropylene monofilaments are made wettable by adding a nonionic surfactant to the monofilaments. In one embodiment this can be done by mixing the surfactant with the polymer before it is extruded, i.e. "internal addition". When this is done, the preferred surfactant is nonionic. The wetting agent is preferably mixed with the polymer in an amount of up to about 5.0 percent by weight of the polymer. In addition, it has been found that with a polymer such as polypropylene, it is beneficial to heat the nonwoven web at some stage to thereby effect migration of the wetting agent to the surface of the monofilaments. In U.S. Pat. Nos. 3,973,068 and 4,070,218 to Weber, the entire disclosures of which are incorporated herein by reference, this heating step is described in detail in relation to the addition of lubricants to a nonwoven web. Naturally, the temperature to which the web is heated should be below the melting point of the monofilaments.

Alternatively, the wetting agent can be applied in a solution to the nonwoven web after it is formed, i.e. "exterior application". This application can be carried out by dipping the nonwoven web into a solution of the wetting agent, after which the solvent is evaporated to thereby leave an amount of the surfactant on the surface of the web. It may also be desirable to heat the web to more quickly evaporate the diluent. Alternatively, the solution of surfactant may be applied to the web by spraying, or by rotogravure printing. In both cases, the evaporation of the diluent may be hastened by heating the web. Naturally, it is desirable for the evaporation to be complete before the web is wrapped on the wind up roll. In all three exterior application methods, the nonionic surfactant is preferred. Also, the nonionic surfactant can be added to thereby constitute up to about 5.0 percent by weight of the web.

Yet another important property of nonwoven liners for diapers and nonwoven webs in general is tensile strength, i.e. the resistance to tearing. This property has been measured by the present inventors on a device which grips a piece of a nonwoven web in a pair of jaws, and then pulls it apart. The force needed to break the web is recorded as the grab tensile strength. This test is typically performed two ways. First, the web is oriented in the jaws so that the force is applied parallel to the direction in which the web was laid down (machine direction, MD). All of the tensile strength results reported herein refer to machine direction pulling.

The inventors were pleased to observe that the nonwoven webs with bilobal shaped monofilaments showed increased tensile strength in both directions over nonwoven webs made from the same material but with circular monofilaments. While not wishing to be bound by any particular theory, it is currently believed that this increased tensile strength may be a result of the increased contact area available between filaments when they are thermally bonded as described above. This is also believed to contribute to the reduction in the bonding temperatures needed to produce a web with sufficient integrity.

Still another property which is important in a nonwoven liner is its opacity or hiding power. That is, it is often desirable that the liner be opaque. It is a known practice in the art to add minor amounts of titanium dioxide to the polymer melt, so as to increase the opacity of the nonwoven web. The inventors have found that the nonwoven webs produced according to the present invention have an increased opacity, possibly due to the increased surface area of the monofilaments which can thereby reflect more light.

Figure 7:
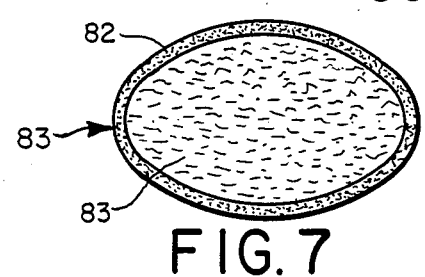
FIG. 7 is a cross section of a catamenial device made with the nonwoven wrap of the present invention.

FIG. 7 shows a cross section through a typical catamenial device such as a feminine napkin 81. As shown, the pad consists of a nonwoven wrap 82 which surrounds an absorbent portion 83. Most of the properties which are desirable for the nonwoven liner for a disposable diaper are likewise desirable to have in the nonwoven wrap for a catamenial device. In particular, it is significant that the present invention provides a nonwoven web with increased softness, i.e. both drapability and smoothness to the touch. Also, it is typically important to enhance the wettability of the wrap 82. This may be done by adding a wetting agent to the wrap by methods such as those described in connection with the diaper liner above. Furthermore, its significant that the present invention provides a nonwoven wrap with improved tensile strength and opacity.

EXAMPLES

Example 1 was run on an apparatus such as that described above. In particular, the web width was 12 inches and the spinneret plate had 40 bilobal shaped orifices per inch of width. Polypropylene was extruded at a melt temperature of about 500° F. The basis weight of the web was 0.8 oz./square yard. The web was bonded together with the pattern shown in FIG. 5a having a bonding area of about 17.5 percent of the web area. In these examples, in order to try different patterns, the webs were bonded off-line, i.e. the webs were formed and wound on a take-up roll. Subsequently, they were unwound on a separate apparatus and bonded. The temperature of the bonding rolls was approximately 270° F.

The resultant web had a Smeltnik Stiffness Test (SST) value of 230 mm. In addition, the web of this example was measured for grab tensile strength by placing a piece of the web between oppositely pulling grippers. The force needed to break the web in the direction at which it was laid down (machine direction or MD) was 15 lbs.

EXAMPLE 2 was run similarly to Example 1 except that the bonding temperature was 240° F. The resultant web had a SST value of 320 mm, and a MD tensile strength of 3.5 lbs.

EXAMPLE 3 was run similarly to Example 1 except that the bonding temperature was 290° F. The resultant web had a SST value of 150 mm, and a MD tensile strength of 5.0 lbs.

EXAMPLE 4 was run similarly to Example 1 except that the bonding pattern was reduced to 10.5%. The resultant web had a SST value of 260 mm, and a MD tensile strength of 12 lbs.

EXAMPLE 5 was run similarly to Example 1 except that the bonding area was 35%. The resultant web had a SST value of 150 mm, and a MD tensile strength of 18 lbs.

EXAMPLE 6 was run similarly to Example 1 except that polyethylene was extruded at about 375° F. through a spinneret plate with about 14 bilobal shaped orifices per inch of width. The basis weight was 0.8 oz./square yard. The web was bonded at about 225° with about 14% bond area. The resultant web had a SST value greater than 700 mm, i.e. the probe fell the full length of the cylinder.

While the invention has been described in connection with specific embodiments thereof, it is evident that many alternatives, modifications, and variations will be apparent to those skilled in the art in light of the foregoing description. In particular, although the nonwoven webs of the invention have been described in connection with liners for disposable diapers and with wraps for catamenial devices, other types of products such as surgical and other disposable garments, industrial wipes, and the like, are clearly contemplated. Accordingly, it is intended to embrace all such applications, alternatives, modifications, and variations as fall within the spirit and broad scope of the appended claims.

What is claimed is:

1. A nonwoven web comprising a plurality of fibers or monofilaments of a thermoplastic material, said monofilaments having a bilobal cross-section.

2. The nonwoven web of claim 1 wherein said thermoplastic material is a polyolefin.

3. The nonwoven web of claim 2 wherein said polyolefin is polypropylene.

4. The nonwoven web of claim 2 wherein said polyolefin is polyethylene.

5. The nonwoven web of claim 2 wherein said polyolefin is an ethylene-propylene copolymer.

6. The nonwoven web of claim 2 wherein said monofilaments or fibers are wettable.

7. The nonwoven web of claim 1 wherein said monofilaments or fibers are wettable.

8. A nonwoven web comprising a plurality of substantially identically prepared continuous and substantially randomly deposited monofilaments of a thermoplastic polymer, said filaments having a bilobal cross-section.

9. The nonwoven web of claim 8 further comprising a degree of interfilament bonding whereby said web is stabilized.

10. The nonwoven web of claim 9 wherein said interfilament bonding comprises a plurality of discrete compacted areas of thermally induced filament bonds extending through a major portion of the thickness of the article, said compacted areas being distributed in an intermittent regular pattern and providing unbonded filament spans therebetween.

11. The nonwoven web of claim 10 wherein the compacted areas constitute from about 10 to about 30 percent of the area of the web.

12. The nonwoven web of claim 10 wherein the compacted areas constitute from about 12 to about 20 percent of the area of the web.

13. The nonwoven web of claim 9 wherein said thermoplastic material is a polyolefin.

14. The nonwoven web of claim 13 wherein said polyolefin is polypropylene.

15. The nonwoven web of claim 13 wherein said polyolefin is polyethylene.

16. The nonwoven web of claim 13 wherein said polyolefin is an ethylene-propylene copolymer.

17. The nonwoven web of claim 9 wherein said monofilaments are wettable.

18. The nonwoven web of claim 9 wherein the length of said cross-section is between about 30 and about 60 microns.

19. The nonwoven web of claim 9 wherein the length of said cross-section is about 40 microns.

20. A nonwoven diaper liner which comprises a plurality of substantially identically prepared continuous and substantially randomly deposited wettable monofilaments of a thermoplastic polymer, said monofilaments having a bilobal cross-section, said liner having a plurality of discrete compacted areas of thermally induced filament bonds extending through a major portion of the thickness of the liner, said compacted areas being distributed in an intermittent pattern providing unbonded filament spans therebetween.

21. The nonwoven diaper liner of claim 20 wherein said thermoplastic polymer is a polyolefin.

22. The nonwoven diaper liner of claim 21 wherein said polyolefin is polypropylene.

23. The nonwoven diaper liner of claim 21 wherein said polyolefin is polyethylene.

24. The nonwoven diaper liner of claim 21 wherein said polyolefin is an ethylene-propylene copolymer.

25. The nonwoven diaper liner of claim 20 wherein the compacted areas constitute from about 10 to about 30 percent of the area of the diaper liner.

26. A nonwoven wrap for a catamenial device which comprises a plurality of substantially identically prepared continuous and substantially randomly deposited wettable monofilaments of a thermoplastic polymer, said monofilaments having a bilobal cross-section, said liner having a plurality of discrete compacted areas of thermally induced filament bonds extending through a major portion of the thickness of the liner, said compacted areas being distributed in an intermittent pattern providing unbonded filament spans therebetween.

27. The nonwoven wrap of claim 26 wherein said thermoplastic polymer is a polyolefin.

28. The nonwoven wrap of claim 26 wherein said polyolefin is polypropylene.

29. The nonwoven wrap of claim 26 wherein said polyolefin is polyethylene.

30. The nonwoven wrap of claim 26 wherein said polyolefin is an ethylene-propylene copolymer.

31. The nonwoven wrap of claim 26 wherein the compacted areas constitute from about 10 to about 30 percent of the area of the wrap.

32. In a multilayer absorbent article which comprises a liner, a fluid-impermeable backing sheet, and an absorbent batt sandwiched therebetween, the improvement comprising employing as the liner a nonwoven web consisting essentially of a plurality of substantially identically prepared continuous and substantially randomly deposited monofilaments of a thermoplastic polymer, said monofilaments having a bilobal cross-section.

33. The improvement of claim 30 wherein said nonwoven web further comprises a degree of interfilament bonding whereby said web is stabilized.

34. The improvement of claim 33 wherein said interfilament bonding comprises a plurality of discrete compacted areas of thermally induced filament bonds extending through a major portion of the thickness of the article, said compacted areas being distributed in an intermittent pattern and providing unbonded filament spans therebetween.

35. The improvement of claim 34 wherein the compacted areas constitute from about 10 to about 30 percent of the area of the web.

36. The improvement of claim 34 wherein the compacted areas constitute from about 12 to about 20 percent of the area of the web.

37. The improvement of claim 32 wherein said thermoplastic polymer is a polyolefin.

38. The improvement of claim 37 wherein said polyolefin is polypropylene.

39. The improvement of claim 37 wherein said polyolefin is polyethylene.

40. The improvement of claim 37 wherein said polyolefin is an ethylene-propylene copolymer.

41. The improvement of claim 32 wherein said monofilaments are wettable.

42. In a process for forming a nonwoven article which comprises:
continuously extruding a thermoplastic polymer through a spinneret having a plurality of orifices to form discrete monofilaments;
drawing the monofilaments;
depositing the monofilaments in a substantially random manner onto a moving carrier to form a web; and
stabilizing the web by interfilament bonding; the improvement comprising the use of a spinneret having bilobal shaped orifices to thereby form monofilaments with a bilobal cross-section.

43. The improvement of claim 40 wherein said interfilament bonding is accomplished by passing said web between a two oppositely rotating rolls, at least one of which is heated, and at least one of which has a raised pattern to thereby form a plurality of discrete compacted areas of thermally induced filament bonds extending through a major portion of the thickness of the web, said compacted areas being distributed in an intermittent pattern corresponding to the raided pattern of the at least one roll and said intermittent pattern providing unbonded filament spans therebetween.

44. The improvement of claim 43 wherein the compacted areas constitute from about 10 to about 30 percent of the area of the web.

45. The improvement of claim 43 wherein the compacted areas constitute from about 12 to about 20 percent of the area of the web.

46. The improvement of claim 42 wherein said thermoplastic polymer is a polyolefin.

47. The improvement of claim 46 wherein said polyolefin is polypropylene.

48. The improvement of claim 46 wherein said polyolefin is polyethylene.

49. The improvement of claim 46 wherein said polyolefin is an ethylene-propylene copolymer.

50. The improvement of claim 42 wherein said monofilaments are made wettable by addition of a wetting agent.

51. The improvement of claim 50 wherein said wetting agent is added to the thermoplastic polymer before extruding.

52. The improvement of claim 51 wherein said wetting agent is a nonionic surfactant.

53. The improvement of claim 51 wherein after stabilizing, the web is heated to cause migration of the wetting agent to the surfaces of the monofilaments.

54. The improvement of claim 50 wherein said wetting agent is applied to the web after stabilizing.

55. The improvement of claim 54 wherein said wetting agent is a nonionic surfactant.

* * * * *